US006475995B1

(12) United States Patent
Roy et al.

(10) Patent No.: US 6,475,995 B1
(45) Date of Patent: Nov. 5, 2002

(54) ORAL DELIVERY OF NUCLEIC ACID VACCINES BY PARTICULATE COMPLEXES

(75) Inventors: Krishnendu Roy, Baltimore; Shau-Ku Huang, Towson, both of MD (US); Hugh Sampson, Larchmont, NY (US); Kam W. Leong, Ellicot City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/232,167

(22) Filed: Jan. 15, 1999

Related U.S. Application Data

(60) Provisional application No. 60/071,679, filed on Jan. 16, 1998.

(51) Int. Cl.[7] .............................................. A61K 48/00
(52) U.S. Cl. ...................... 514/44; 424/489; 424/492; 424/497; 424/499; 435/320.1; 435/455
(58) Field of Search ................................ 424/489, 492, 424/497, 499, 439; 514/44; 435/320.1, 455; 536/23.1

(56) References Cited

U.S. PATENT DOCUMENTS

| | | | | |
|---|---|---|---|---|
| 5,674,495 A | * | 10/1997 | Bowersock et al. | 424/184.1 |
| 5,783,567 A | * | 7/1998 | Hedley et al. | 514/44 |
| 5,858,989 A | * | 1/1999 | Babiuk et al. | 514/44 |
| 5,880,103 A | * | 3/1999 | Urban et al. | 514/44 |
| 5,935,568 A | * | 8/1999 | Dow et al. | 424/93.21 |
| 5,972,707 A | * | 10/1999 | Roy et al. | 435/455 |
| 5,990,091 A | * | 11/1999 | Tartaglia et al. | 514/44 |
| 6,024,983 A | * | 2/2000 | Tice et al. | 424/501 |
| 6,025,337 A | * | 2/2000 | Truong et al. | 514/44 |

FOREIGN PATENT DOCUMENTS

| WO | 96 00295 A | 1/1996 |
|---|---|---|
| WO | 98 1162 A | 1/1998 |

OTHER PUBLICATIONS

Database Embasse, AN 1999232955, Li et al. (Journal of Immunology, 162,5, pp. 3045–3052, 1999), Abstract.*

Cryz et al. (Vaccine, vol. 14, 7, Vaccine Delivery Systems, Reports of the Expert Panels, pp. 665–688) 1996*

McCluskie et al. (Molecular Medicine, 5, pp. 287–300, 1999).*

Taber's Cyclopedic Medical Dictionary (edition 17, 1993).*

Webster' Ninth New Collegiate Dictionary (1990).*

Mao G–Q et al, ."DNA–Chitosan Nanospheres for Gene Delivery" Proceedings of the International Symposium on Controlled Released Bioactive Materials, Jul. 7, 1996, pp. 401–402.

Walsh S.M. et al. "Combination of drug and gene delivery of gelatin nanospheres for the treatment of cystic fibrosis" Proceedings of the 24th. International Symposium on Controlled Release of Bioactive Materials, Jun. 15, 1997 pp. 75/76.

Tuong–Le V.L. et al. "Delivery of DNA Vaccine Using Gelatin–DNA Nanospheres" Proceedings of the 24th. International Proceedings of the 24th. International Symposium on Controlled Release of Bioactive Materials, Symp. 24, Jun. 15, 1997, pp. 39/40.

Roy, Krishendu et al. "Oral immunization with DNA chitosan nanospheres" Proc. Int. jSymp. Controlled Release Bioact. Mater. (1998), 25th 348–349.

* cited by examiner

*Primary Examiner*—Dave T. Nguyen
(74) *Attorney, Agent, or Firm*—Banner & Witcoff, Ltd.

(57) ABSTRACT

Nanoparticle coacervates of nucleic acids and polycations serve as effective vaccines when administered orally. They can induce immunity to a variety of disease causing agents and raise a protective response to allergens.

6 Claims, 11 Drawing Sheets

TEM: Scale Bar = 210 nm

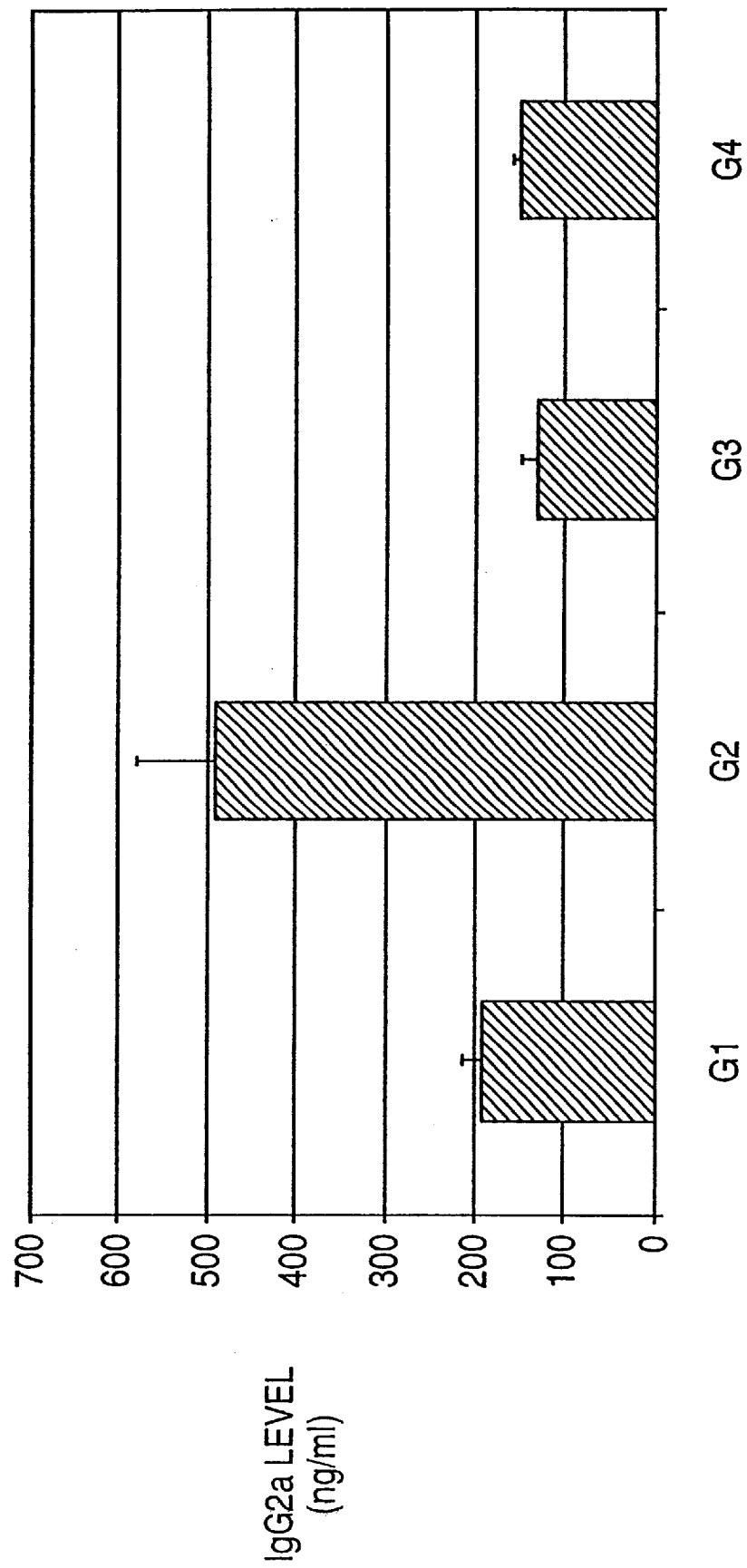

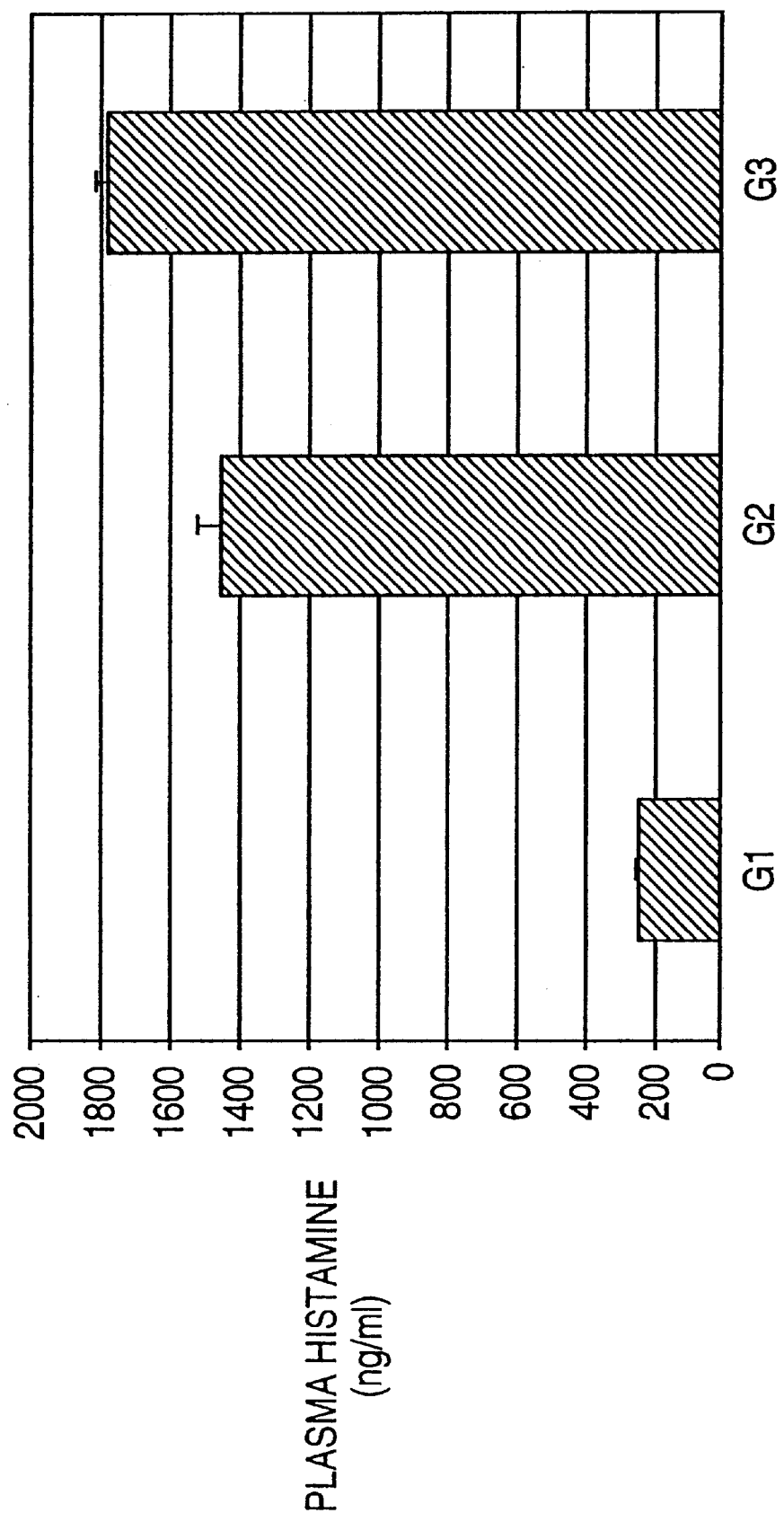

ORAL DELIVERY OF NUCLEIC ACID VACCINES BY PARTICULATE COMPLEXES

RELATED APPLICATION

This application claims the benefit of Provisional Application Ser. No. 60/071,679, filed Jan. 16, 1998.

TECHNICAL FIELD OF THE INVENTION

This invention is related to the field of immunology and allergic diseases. In particular it relates to the area of food allergies.

BACKGROUND OF THE INVENTION

IgE is critical in the pathogenesis of various allergic diseases, including type I immediate hypersensitivity (1), and the best-characterized food-allergic responses involve IgE-mediated responses (2). A failure to develop, or a breakdown in, oral tolerance results in the production of food-specific IgE Abs. IgE Abs and allergens activate mast cells and basophils through the high affinity IgE receptor (Fce RI), and systemic anaphylactic reaction are provoked by histamine and other mediators released from activated mast cells and basophils (3). Numerous clinical and experimental animal studies have indicated the pivotal role of T cells and cytokines in the development of IgE-associated allergic diseases (4–5). In particular, a subset (Th2) of T cells, which has been distinguished functionally by its pattern of cytokine secretion, is thought to play a key role. Th2 cells are thought to promote allergic responses through their secretion of the cytokines,IL-4 and IL5, which promote IgE production and mast cell development, and eosinophilia, respectively. Cytokines released by the opposing pathway (Th1), such as IFN-γ, inhibit the development and expansion of Th2 cells and cytokine production. These studies demonstrate the importance of cytokines in the regulation of Th2 responses, and suggest potential therapeutic approaches to modify the development of IgE- and Th2-associated phenotypes.

Food allergy (including allergic reactions to nuts, egg, milk, and seafood) is a major health problem because of the potential severity of allergic reactions, the nature of the allergic hypersensitivity, and the ubiquitous use of food products. Recent surveys in the US determined that food allergies are the most common single cause of anaphylaxis treated in hospital emergency departments (6, 7). In both reports, food-induced anaphylaxis accounted for about one-third of anaphylactic cases, with peanuts and tree nuts accounting for the majority of reactions to foods. It is believed that about 100 fatal cases of food-induced anaphylaxis occur in the US each year (8), that peanuts are one of the leading causes of food-allergic reactions (9, 10), and that peanuts and tree nuts together represent the leading cause of fatal and near-fatal food-induced anaphylaxis (6, 8, 11–12).

While food allergy has become recognized as an increasing national health problem, the only proven treatment of food allergy consists of educating the patient in the complete avoidance of all possible sources of food allergens. However, frequent accidental ingestions [up to 50% of peanut allergic patients per year (13–14)] occur due to the ubiquitous use of peanut protein in a variety of food products. Two small trials with standard rush immunotherapy for peanut allergy demonstrated limited efficacy and unacceptable side effects (15). Given the large number of patients with potentially fatal food allergy, the extreme difficulty in avoiding all food allergen exposure, and the lack of efficacy for standard immunotherapy, novel and effective therapeutic strategies are urgently needed.

Utilizing a combination of oral and intraperitoneal (i.p.) sensitizations, we have recently shown that C3H mice develop peanut-specific IgE Abs and experience systemic anaphylaxis upon challenge with peanut proteins (16). We demonstrated that mice sensitized orally with peanut proteins (PN) followed by i.p. challenge with PN exhibit similar features observed in allergic patients, including active systemic anaphylaxis such as itching and pilar erecti; and with sensitization using combined oral feeding and i.p. injection with adjuvants [cholera toxin (CTx) and alum, respectively], the more severe symptoms including death were induced. Several parameters of the hypersensitivity response in mice can be monitored, including symptom scores, levels of serum specific IgE, and challenge-induced changes in plasma histamine, mast cell degranulation and vascular leakage. As a corollary, Snider et al. (17) demonstrated that oral sensitization of mice followed by i.p. challenge with hen egg lysozyme or OVA in the presence of CTx results in fatal systemic anaphylaxis in 80% of sensitized mice. The fatality was associated with elevated levels of plasma histamine and degranulated mast cells in a number of target organs. The finding that a more severe anaphylactic reaction is seen in mice sensitized and challenged with Ag and CTx as an adjuvant is consistent with recent studies demonstrating that CTx can promote Th2-type responses (18–19). These studies further suggest an important role for Ag-induced IgE and Th2 responses in the development of hypersensitivity, and provide a useful model to examine the regulatory mechanisms of peanut-induced hypersensitivity, and to explore the utility of the DNA-based immunization approach.

Recent advances in the manipulation of the immune system utilizing "DNA-based immunization" has provided an important and novel therapeutic approach in a variety of human diseases (20). DNA-based immunization has been used to generate and/or modify the host immune response, with the ultimate purpose of preventing, reversing, stabilizing, or slowing down the progression of disorders. This approach in manipulating the immune system has generated great interest by investigators searching for novel approaches to protect the host against various diseases (21–24). Injection of "naked" plasmid DNA (PDNA) encoding Ag results in long-lasting cellular and humoral immune responses to Ag (25). Successful immunization has been demonstrated with administration of pDNA by intramuscular, intradermal, intravenous, and subcutaneous routes (20, 26–28). It has been reproducibly demonstrated that intramuscular injection of pDNA provoke long-term immune responses characterized by the synthesis of specific IgG Abs, and by the efficient generation of CD8+cytotoxic T cells and CD4+Th1 cells (29). Recent results have also indicated that the pDNA persists episomally without replication or incorporation into the host cell genome (20). These new and exciting developments thus show promise of safe and effective therapy for various diseases.

Using intramuscular gene delivery, Hsu et al (30–31) have recently demonstrated that intramuscular injection of rats and mice with a pDNA encoding a house dust mite allergen (Der p 5) prevent the induction of IgE synthesis, histamine release, and airway hyper responsiveness in animals challenged with aerosolized allergen. Raz et al. (32) showed that β-galactosidase (β-gal)/alum-primed Balb/c mice immunized intradermally with pDNA encoding β-gal show a 66–75% reduction in the level of β-gal-specific IgE in 6 weeks. Also this pDNA immunization protocol induced specific IgG2a, and IFN-γ secretion by the Th cells in the β-gal/alum-primed mice. However, despite the recent success of DNA-based immunization in altering the IgE- and Th2-associated immune response in various models, the prophylactic and/or therapeutic potentials are far from clear, and better, more efficient, and safer gene transfer and gene expression system by using improved DNA delivery systems are urgently needed.

Gene therapy continues to hold exciting promise in treating many genetic disorders [36,37]. Recent clinical trials indicate that an efficient and safe delivery vehicle remains a crucial barrier to successful gene therapy [38]. Viral and retroviral vectors have been the most efficient and commonly used delivery modalities for in vivo gene transfer [39–41]. However, issues of immune response to viral proteins remain to be addressed. Non-viral delivery systems have been increasingly proposed as alternatives to viral vectors because of potential advantages such as ease of synthesis, cell/tissue targeting, low immune response, and unrestricted plasmid size.

The most promising non-viral gene delivery system thus far, other than the "gene gun" in DNA vaccine applications, comprises ionic complexes formed between DNA and polycationic liposomes [42–45]. Factors hindering the success of the liposomal approach appear to be instability of the complex, toxicity of the cationic lipid, and short half-life of the complexed DNA. Held together by electrostatic interaction, these complexes may dissociate because of the charge screening effect of the polyelectrolytes in the biological fluid. A strongly basic lipid composition can stabilize the complex, but such lipids may be cytotoxic. The fact that the DNA is coated on the outside of the liposome renders the DNA vulnerable to nuclease degradation in transit from site of administration. to the nucleus of the target cell. A recent pharmacokinetic study shows that a HLA-B7 gene, when delivered by DC-Chol/DOPE intravenously, has a half-life of less than five minutes, and becomes undetectable after one hour [46]. No encoded protein could be detected in tissues harboring the residual plasmid by immunohistochemical analysis at 1 or 7 days post-injection. This poor bioavailability is not too surprising in light of similar instability which is characteristic of many therapeutic proteins. For example, interferons and several other cytokines also have plasma half-lives in the order of minutes. The therapeutic potential of many of these delicate polypeptides has been improved by controlled release formulations.

Complex coacervation is a process of spontaneous phase separation that occurs when two oppositely charged polyelectrolytes are mixed in an aqueous solution. The electrostatic interaction between the two species of macromolecules results in the separation of a coacervate (polymer-rich phase) from the supernatant (polymer-poor phase). This phenomenon can be used to form microspheres and encapsulate a variety of compounds. The encapsulation process can be performed entirely in aqueous solution and at low temperatures, and has a good chance, therefore, of preserving the bioactivity of the encapsulant. In developing an injectable controlled release system, we have used the complex coacervation of gelatin and chondroitin sulfate to encapsulate a number of drugs and proteins [47]. Cytokines have been encapsulated in these microspheres for cancer vaccination [48]. Anti-inflammatory drugs have also been incorporated for intra-articular delivery to the joints for treating osteoarthritis [49]. It occurred to us that we could replace chondroitin sulfate with DNA as the polyanion to form microspheres with gelatin or other polycations.

Gelatin, the denatured form of collagen, is a polyampholyte which gels below 35–40° C. It is widely used in food (55%), pharmaceutical (25%), and photographic (15%) industries [50]. At pH below 5, it is positively charged and can complex with DNA to form a coacervate. After crosslinking, the coacervate is stable in solution of high ionic strength. Chitosan is a bioabsorbable, non-toxic, polysaccharide with low. immunogenicity. The polysaccharide has an average amino group density of 0.837 per disaccharide unit. It has been proposed as a matrix for controlled release microsphere formulation and as a stabilizer for alginate capsules encapsulating cells.

SUMMARY OF THE INVENTION

It is an object of the present invention to provide a vaccine preparation suitable for oral administration.

It is another object of the present invention to provide a method of immunizing a mammal by ingestion of the vaccine.

These and other objects of the invention are achieved by providing a vaccine formulation which is suitable for oral ingestion. The vaccine comprises a solid nanoparticle of less than 5 μm comprising a coacervate of a polymeric polycation and a polyanion, wherein the polyanion consists of nucleic acids encoding an antigen. A pharaceutically acceptable vehicle may be used as a carrier.

According to another embodiment a method is provided of vaccinating a mammal against an antigen. The method comprises: orally administering a vaccine formulation comprising a solid nanoparticle of less than 5 μm. The nanoparticle comprises a coacervate of a polymeric polycation and a polyanion. The polyanion consists of nucleic acids encoding an antigen.

These and other embodiments provide the art with new tools for simply and effectively vaccinating people and other mammals against inter alia viral, parasitic, fungal, and bacterial diseases. Environmental and food allergens can also be used as the antigens.

BRIEF DESCRIPTION OF THE DRAWINGS

FIG. 3.

FIG. 4. Beta-galactosidase expression in mouse stomach and small intestine 5 days after oral delivery of LacZ gene. Mice were sacrificed and the stomach and small intestine were surgically removed, stained for LacZ using X-gal and photographed as described in Materials and Methods.

FIG. 5. FIG. 5b. shows serum anti-Arah-2 IgG2a levels before sensitization (4 weeks after first immunization). Blood was collected from tail veins and the serum was assayed using Arah-2 specific ELISA (anti-DNP mAb IgG2a as standards as described in Methods). Each Bar represents pooled samples from 5 mice (2 for non-immunized) measured in duplicate.

In all figures G1: Mice immunized with chitosan-pArah2 nanoparticles (single dose). G2: Mice immunized with two doses (one week apart) of chitosan-DNA nanoparticles. G3: Mice immunized with naked pArah2. G4: Non-immunized mice.

Figure 6:
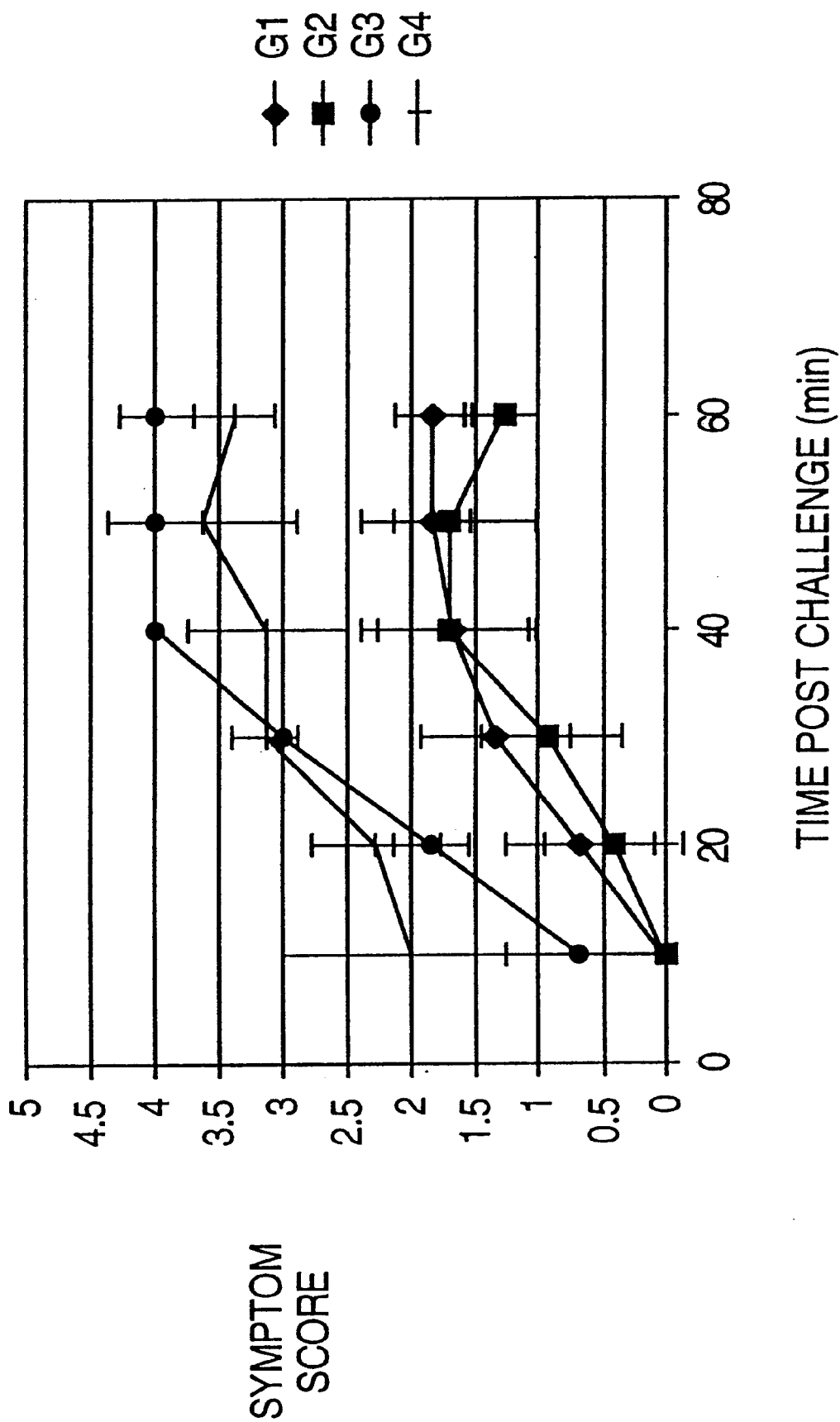

FIG. 6. Average anaphylactic response (from two separate experiments) of six mice following Arah2 challenge. Control and chitosan-pArah2 nanosphere-immunized mice were sensitized 3 times, one-week apart, with oral and i.p. doses of crude peanut extract. Following sensitization, mice were challenged i.p. with 200 μg/mouse of recombinant Arah2 protein and examined for anaphylactic response over a period of time as indicated. Anaphylaxis was classified by the following scoring system: 0, no sign of reaction; 1, scratching and rubbing around the nose and head; 2, decreased activity with an increasing respiratory rate, pilar erect and/or puffing around the eyes; 3, labored respirations, cyanosis around the mouth and tail; 4, slight or no activity after prodding or tremors, convulsion; 5, death. G1: Mice immunized with chitosan-pArah2 nanoparticles (single dose). G2: Mice immunized with two doses (one week apart) of chitosan-DNA nanoparticle. G3: Mice immunized with naked pArah2. G4: Non-immunized mice.

Figure 7B:
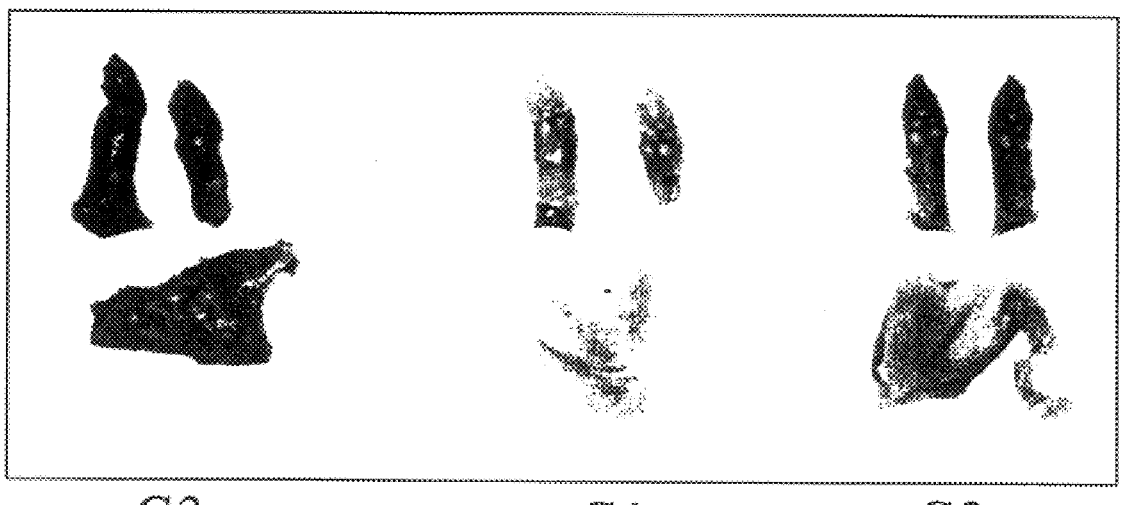

FIG. 7. FIG. 7a. shows levels of plasma histamine (average of 2 mice) in immunized or control mice following sensitization and challenge (as described in Methods). 10–15 min following challenge blood was collected from the optic artery and the plasma was assayed for histamine levels using a competitive ELISA based histamine kit (Immunotech Inc., USA). FIG. 7b. shows vascular leakage assay: Immunized and control mice were injected with 200 μl of Evan's blue immediately prior to challenge. Intraperitoneal challenge with Arah2 was performed as described in Materials and methods and mice were monitored for vascular leakage in the extremities. Blue color (G3, naked DNA immunized) in peripheral tissues indicate dye leakage through the vascular bed due to increased capillary permeability as a result of anaphylactic or allergic response. Absence of blue color (G1 and G, chitosan-pArah-2-nanosphere immunized mice with or without boost) indicates absence of anaphylactic vascular leakage.

DETAILED DESCRIPTION

The disclosures of prior U.S. patent applications Ser. Nos. 08/265,966, and 08/657,913 are expressly incorporated herein.

Our novel approach of using DNA nanospheres for oral administration has demonstrated the general utility of oral DNA-based immunization. The induced response may be either or both humoral or cellular. It may be used for inducing any type of immune response desired. This may be against bacterial, viral, fungal, parastic, or tumor-associated antigens.

Any type of expression construction can be used to obtain expression in the vaccinated mammal of the antigen gene. Typically the gene will be operably linked to a promoter which is active in the recipient cells. Viral promoters, such as CMV are particularly useful for this purpose, although any known promoter can be used. The gene or oligonucleotide encoding the antigen can be in the form of RNA, DNA, cDNA.

The antigen can be any known in the art, including but not limited to an allergen, particularly a food allergen, or a bacterial, viral, fungal, parastic, or tumor-associated antigen.

The crucial aspect of the invention is the administration of the vaccines by the oral route. Thus the formulation may be any which is safe and healthy for oral ingestion. Preferably the formulation contains no toxic substances. If in a liquid form, sterility may be desired. The form of the vaccine may be as a tablet, capsule, liquid, elixir, powder, granules, etc. It may be admixed with food or drink. It may self-adminstered for added convenience rather than requiring the expense of a health professional for administration as is often required for injections and other inocculations.

It is preferred that the nanospheres be less than 5 microns. More preferred are nanospheres of less than 3 microns, and even more proffered are nanospheres which are less than 2, 1, 0.5, and 0.1 microns. While size can be effected by the conditions of coacervation and the size of the component polyanion and polycation, nanospheres of the desired size can also be size selected using a technique which separates the nanospheres on the basis of size. The particles can be size-fractionated, e.g., by sucrose gradient ultracentrifugation. Particles with size less than 150 nanometers can access the interstitial space by traversing through the fenestrations that line most blood vessels walls.

The polymeric polycation from which the coacervate is formed can be any which is biologically degradable, and safe for oral ingestion. This includes, but is not limited to gelatin and chitosan. Polyamino acids, synthetic or naturally occurring, can also be used, such as polylysine, poly-lysine-poly-arginine, polyarginine, protamine, spermine, spermidine, etc. Polysaccharides may also be used.

Targeting ligands, if desired, can be directly bound to the surface of the nanosphere or can be indirectly attached using a "bridge" or "spacer". Because of the amino groups provided by the lysine groups of the gelatin, the surface of the nanospheres can be easily derivatized for the direct coupling of targeting moieties. For example, carbo-diimides can be used as a derivatizing agent. Alternatively, spacers (linking molecules and derivatizing moieties on targeting ligands) such as avidin-biotin can be used to indirectly couple targeting ligands to the nanospheres. Biotinylated antibodies and/or other biotinylated ligands can be coupled to the avidin-coated nanosphere surface efficiently because of the high affinity of biotin ($k_a \sim 10^{15}$ $M^{-1}$) for avidin (Hazuda, et al., 1990, Processing of precursor interleukin 1 beta and inflammatory disease, *J. Biol. Chem.*, 265:6318–22; Wilchek, et al., 1990, Introduction to avidin-biotin technology, *Methods In Enzymology*, 184:5–13). Orientation-selective attachment of IgGs can be achieved by biotinylating the antibody at the oligosaccharide groups found on the $F_c$ portion (O'Shannessy, et al., 1984, A novel procedure for labeling immunoglobulins by conjugation to oligosaccharides moieties, *Immunol. Lett.*, 8:273–277). This design helps to preserve the total number of available binding sites and renders the attached antibodies less immunogenic to $F_c$ receptor-bearing cells such as macrophages. Spacers other than the avidin-biotin bridge can also be used, as are known in the art. For example, Staphylococcal protein A can be coated on the nanospheres for binding the $F_c$ portions of immunoglobulin molecules to the nanosphetes.

Cross-linking of linking molecules or targeting ligands to the nanosphere is used to promote the stability of the nanosphere as well as to covalently affix the linking molecule or targeting ligand to the nanosphere. The degree of cross-linking directly affects the rate of nucleic acids released from the nanospheres. Cross-linking can be accomplished using glutaraldehyde, carbodiimides such as EDC (1-ethyl-3-(3-dimethylaminopropyl)-carbodiimide, DCC (N,N'-dicyclohexylcarbodiimide), carboxyls (peptide bond) linkage, bis (sulfosuccinimidyl) suberate, dimethylsuberimidate, etc.

Targeting ligands according to the present invention are any molecules which bind to specific types of cells in the body. These may be any type of molecule for which a cellular receptor exists. Preferably the cellular receptors are expressed on specific cell types only. Examples of targeting ligands which may be used are hormones, antibodies, cell-adhesion molecules, saccharides, drugs, and neurotransmitters.

The nanospheres of the present invention have good loading properties. Typically, following the method of the present invention, nanospheres having at least 5% (w/w) nucleic acids can be achieved. Preferably the loading is greater than 10 or 15% nucleic acids. Often nanospheres of greater than 20 or 30%, but less than 40 or 50% nucleic acids can be achieved. Typically loading efficiencies of nucleic acids into nanospheres of greater than 95% can be achieved.

The method of the present invention involves the coacervation of polymeric cations and nucleic acids. Because this process depends on the interaction of the positively charged polymeric cations and the negatively charged nucleic acids it can be considered as a complex coacervation process. However, sodium sulfate (or ethanol) induces the coacervation reaction by inducing a phase transition, and therefore it could also be considered as a simple coacervation reaction. Nucleic acids are present in the coacervation mixture at a concentration of between 1 ng/ml to 500 µg/ml. Desirably the nucleic acids are at least about 2–3 kb in length. Sodium sulfate is present at between 7 and 43 mM. Gelatin or other polymeric cation is present at between about 2 and 7% in the coacervation mixture.

Nanosphere delivery vehicles synthesized by the complex coacervation of DNA with either gelatin or chitosan have several potential attractive features: 1) ligands may be conjugated to the nanosphere for targeting or stimulating receptor-mediated endocytosis; 2) lysosomolytic agents can be incorporated to reduce degradation of the DNA in the endosomal and lysosomal compartments; 3) other bioactive agents or multiple plasmids can be co-encapsulated; 4) bioavailability of the DNA can be improved because of protection from serum nuclease degradation by the matrix; 5) the nanosphere can be lyophilized for storage.

An attractive nanosphere delivery system requires a delicate balance among factors such as the simplicity of preparation, cost effectiveness, nucleic acids loading level, controlled release ability, storage stability, and immunogenicity of the components. The gene delivery system described here may offer advantages compared to other particulate delivery systems, including the liposomal system. The problems of instability, low loading level, and controlled release ability are better resolved with the polymeric nanosphere systems. Gelatin has received increasing biologic use ranging from surgical tissue adhesive (Weinschelbaum, et al., 1992, Surgical treatment of acute type A dissecting aneurysm with preservation of the native aortic valve and use of biologic glue. Follow-up to 6 years, *J. Thorac. Cardiovasc. Surg.*, 130:369–74) to quantitative immunohistochemical assays (Izumi, et al., 1990, Novel gelatin particle agglutination test for serodiagnosis of leprosy in the field, *J. Clinical Microbiol.*, 28:525–9) and as drug delivery vehicle (Tabata, et al., 1991, Effects of recombinant alpha-interferon-gelatin conjugate on in vivo murine tumor cell growth, *Cancer Res.*, 51:5532–8), due to its biocompatibility and enzymatic degradability in vivo. Compared to other synthetic polymeric systems, such as the extensively studied polylactic/polyglycolic copolymers, the mild conditions of nanosphere formulation are appealing. Unlike the solvent evaporation and hot-melt techniques used to formulate synthetic polymeric nanospheres, complex coacervation requires neither contact with organic solvents nor heat. It is also particularly suitable for encapsulating bio-macromolecules such as nucleic acids not only through passive solvent capturing but also by direct charge-charge interactions.

Unlike viral vectors, which cannot deliver genes larger than 10 kb, the nanosphere delivery system of the present invention does not have such size limitations. Nucleic acid molecules of greater than about 2 kb can be used, and nucleic acid molecules even greater than 10 kb may be used. Typically the nucleic acid will be greater than 300 bases, and typically greater than 0.5, 1, 2, 5, or 10 kb. Typically the nucleic acid molecule will be less than 200, 100, or 50 kb.

The above disclosure generally describes the present invention. A more complete understanding can be obtained by reference to the following specific examples which are provided herein for purposes of illustration only, and are not intended to limit the scope of the invention.

We have evaluated the modulation of peanut allergen (as a model allergen)-induced hypersensitivity using an oral chitosan/DNA-based immunization approach. The model for this study is the hypersensitivity responses to peanut allergens in an inbred strain of mice (C3H), in which several quantitative parameters of hypersensitivity have been established, and a significant induction of the immune response has been demonstrated following gene immunization. This system demonstrates that antigens can be delivered to the systemic circulation of the animal by oral administration of a DNA.

EXAMPLE 1

Materials: Approximately 6–7 weeks old inbred strains of C3H and AKR/J mice were purchased from Charles River Laboratories, Massachusetts. Plasmid encoding the peanut allergen Arah2 (pArah2) was grown in a large scale by PEG method. High molecular weight chitosan (C390, Mw ~390,000) and low molecular weight chitosan (PCL113, Mw ~60,000–100,000) were used as the polycation to complex with the DNA.

Gene expression construct: pCR3Arah2: Burks et al (33–34) have identified two major protein fractions in peanuts, Ara h1 (63.5 kD) and Ara h2 (17 kD), and over 95% of peanut allergic patients are sensitive to these proteins. We have generated an Ara h2 gene construct, pCR3Arah2 in an expression vector (pCR3). A PCR-amplified Ara h2 coding region gene segment with the addition of a Kozak consensus translation codon was ligated into pCR3 expression vector containing CMV promoter sequence.

Nanosphere preparation: Briefly, DNA-chitosan nanospheres were prepared as described previously. Briefly, a 0.02% solution of chitosan (pH 5.7 in NaAc-HOAc buffer) is vortexed with a 50 ug/ml DNA solution in 50 mM Sodium Sulfate at 55° C. for 15–20 seconds. For the low molecular weight chitosan the concentration was changed to 0.04% in deionized water (pH adjusted to 5.7) and the salt concentration was 5 mM Sodium Sulfate.

Oral delivery: All nanospheres were prepared fresh before administration and kept at room temperature. Un-anesthetized mice were fed different formulations of nanospheres and "naked" DNA at a dose of 50 ug DNA per mice. Feeding (intra-gastric delivery) was performed using a 1 ml syringe fitted with an animal feeding needle (Fisher Scientific, USA). The feeding volume was 1 ml for each mice.

Experimental. Protocols: The study was divided into two experiments: the first to examine the immune response at different time points after vaccination and the second to study the protection efficacy of the immunization protocol. In the first study the experimental groups were as follows: Group 1: Single dose of high molecular weight chitosan-pArah2 nanospheres, Group 2: One dose of high molecular weight chitosan-pArah2 nanospheres followed by a booster shot after 2 weeks, Group 3: Single dose of low molecular weight chitosan-pArah2 nanospheres, Group 4: One dose of low molecular weight chitosan-pArah2 nanospheres followed by a booster shot after 2 weeks, Group 5: Naked DNA (pArah2), Group 6: Single dose of low molecular weight chitosan-pEGFP (plasmid encoding the firefly green fluorescence protein, Clontech Inc, USA) nanospheres and Group 7: Naive mice fed with phosphate buffered saline (PBS). In the second experiment the study groups were: Group 1: One dose of high molecular weight chitosan-pArah2 nanospheres followed by a booster shot after 2 weeks, Group 2: One dose of low molecular weight chitosan-pArah2 nanospheres followed by a booster shot after 2 weeks, Group 3: Single dose of low molecular weight chitosan-pArah2 nanospheres, Group 4: naive mice fed with PBS.

Sample collections and measurements: For the first study serum and fecal extracts were collected at different time points after the first immunization. Briefly, for serum collection, 1 φul of blood was collected from the tail vein of each mice, clotted at room temperature for one hour and then centrifuged at 1000 rpm for 25 min. The resulting supernatant (serum) was stored at −80° C. till antibody measurements were performed. For fecal extracts, one or two drops of fresh fecal pellets were collected, weighed and dissolved in PBS (100 mg/ml). The debris were centrifuged at 14,000 rpm for 25 min and the supernatant was stored at −80° C. for measurements. Anti-Arah2 specific IgG or IgA levels in serum and fecal extract were measured using an antigen specific ELISA (Enzyme linked Immuno-sorbent Assay). Microtiter plates were coated overnight with 10 ug/ml (100 ul) of purified Arah2 protein in sodium carbonate-bicarbonate buffer. Plates were blocked for 2 hrs in room temperature with 4% bovine serum albumin, 2% normal goat serum in PBS and then incubated with serial dilutions of serum or fecal extract for 18 hrs following the incubation, biotinylated anti-IgG or anti-IgA added to the wells for 1 hr at 37° C. The plates were then incubated with HRP conjugated streptavidin for 30 min at room temperature and developed with o-phenyladeneline (OPD). Absorbances were read at 490 nm using a microplate reader (Bio-Rad Lab., USA). IgG titers were measured by coating the plates with different concentrations of mouse IgG followed by the biotinylated antibody and subsequent steps. IgA data was expressed as O.D. values.

Challenge and protection study: Two weeks following the booster dose i.e., four weeks after the first immunization all mice were sensitized orally and intra-peritoneally with crude peanut extracts. Sensitization was performed 3 more times one week apart. Following sensitization, mice were challenged intra-peritoneally with 1 mg of purified Arah2 protein and anaphylactic response was observed and graded as described below. Peanut-induced hypersensitivity in C3H mice:

An inbred strain of mice, C3H, has been shown to exhibit immediate hypersensitivity following sensitization with OVA together with CTx as an adjuvant (17). To examine the effect of oral sensitization of C3H mice with peanut allergen extracts (PN), we have performed studies using various sensitization protocols, and developed quantitative parameters for measuring PN-induced hypersensitivity (16). Symptoms of anaphylaxis became apparent in mice 5 to 10 min, peaked at 30 to 50 min, after Ag challenge. The severity of symptoms was determined by observing mouse behavior post-challenge, and was scored by their responses to stimuli such as mild prodding. Anaphylaxis was classified by the following scoring system: 0, no sign of reaction; 1, scratching and rubbing around the nose and head; 2, decreased activity with an increasing respiratory rate, pilar erecti and/or puffing around the eyes; 3, labored respirations, cyanosis around the mouth and tail; 4, slight or no activity after prodding or tremors, convulsion; 5, death. This scoring system was established based on our previous experiments and a modified scoring system used previously (35).

Figure 1:
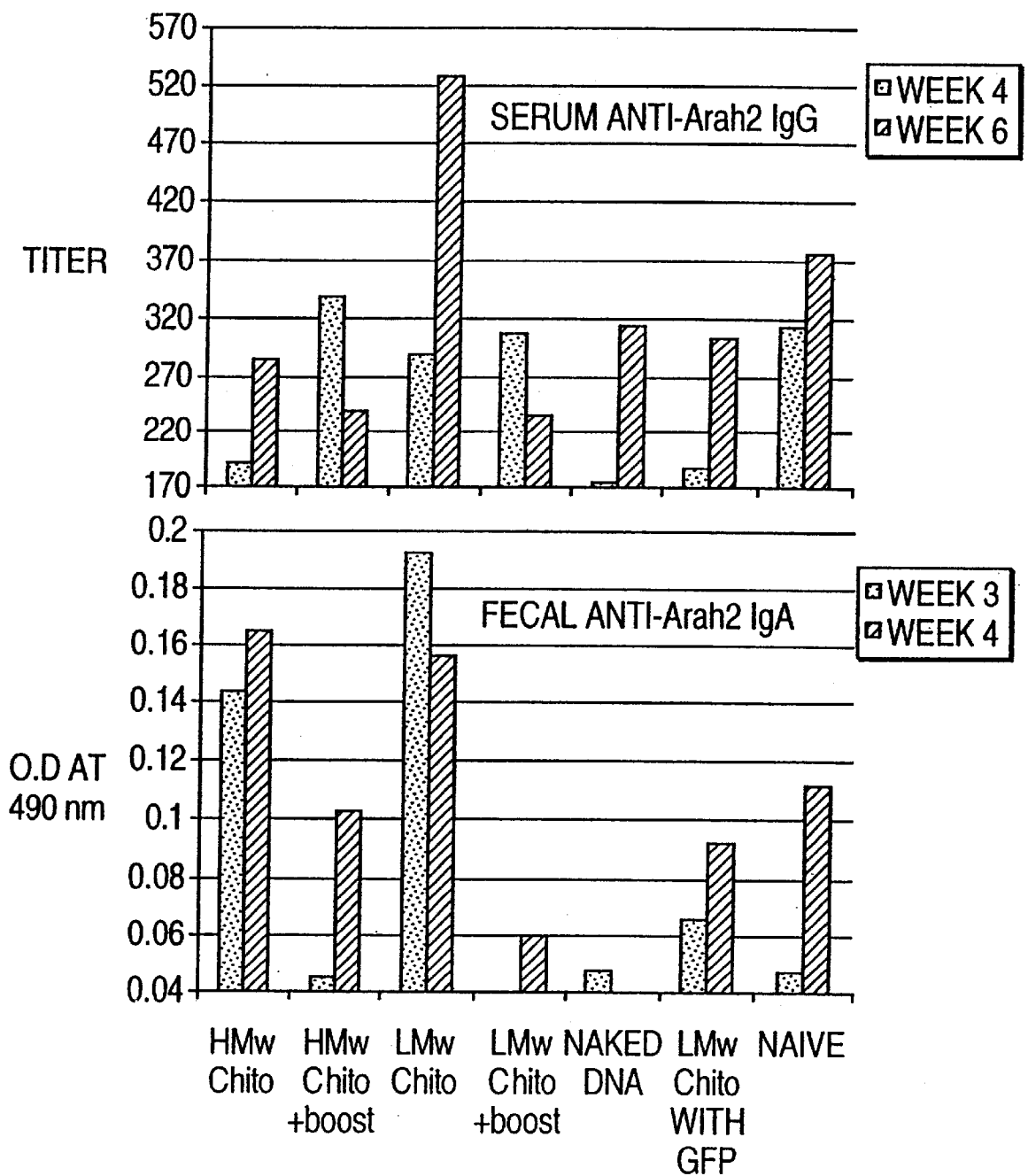
FIG. 1. Immune response in AKR/J mice orally immunized with various formulations of DNA-chitosan nanospheres and naked DNA encoding the Peanut allergen. Top panel: IgG response in serum 4 and 6 weeks after immunization. Purified mouse IgG was used as standard to calculate titer (ng). Bottom Panel: IgA response in fecal extract 3 and 4 weeks after immunization. O.D valuse at 490 nm is reported here for undiluted sample (supernatant of 100 mg/ml fecal pellets dissolved in PBS). Each bar represents values of pooled samples from eight animals (five in case of negative controls).
Figure 2:
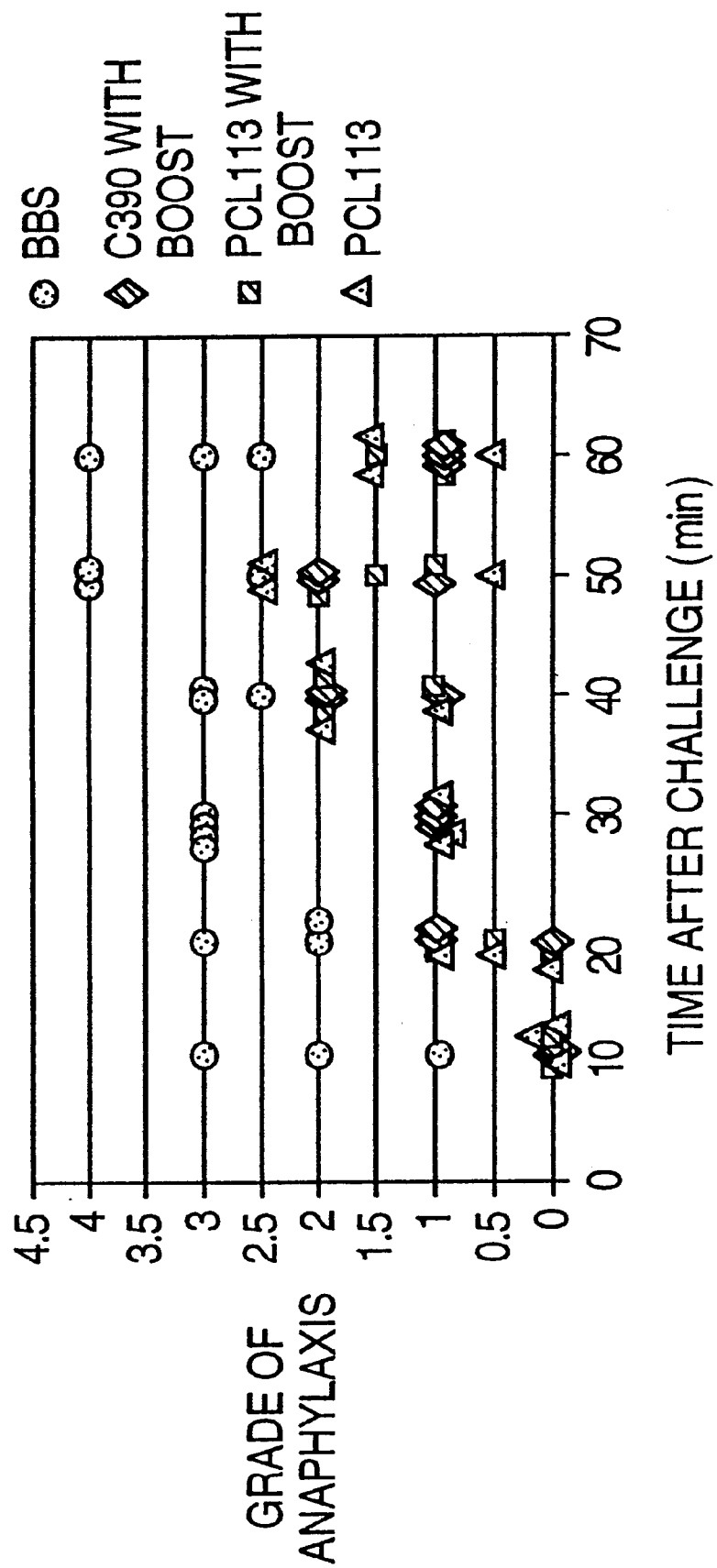
FIG. 2. Protection Studies. Sham-fed and pArah2-nanospheres immunized AKR/J mice were sensitized four times, one week apart, with oral and intra-peritoneal doses of crude peanut extract. Following sensitization the mice were challenged with 1 mg/mice intra-peritoneal dose of pure Arah2 protein and examined for anaphylactic response over a period of time. Right panel: Grade of anaphylaxis of mice over a period of one hour. Left panel: Comparison of different groups 30 minute after challenge. C390=High molecular weight chitosan. PCL113=Low molecular weight chitosan. Each circle represents one mouse.

Results in FIG. 1 shows that there were positive antibody responses in groups immunized by the DNA nanospheres. Most importantly, the hypersensitivity study shows that significantly improved response in terms of symptoms of anaphylaxis in mice immunized by the DNA nanospheres (FIG. 2).

EXAMPLE 2

Materials

Chitosan (Mw ~390,000) was purchased from Vansen Inc., WA, USA. To generate an expression gene construct containing a major peanut allergen gene, Arah2, a PCR-amplified Arah2 coding region gene segment (kindly provided by Dr. G. Bannon, University of Arkansas) with the addition of a Kozak consensus translation codon was ligated into pCR3 expression vector containing CMV promoter/enhancer sequences. The resultant expression construct was designated as pCMV Arah2. Plasmid encoding β-galactosidase (p43LacZ) was a gift from Dr. Barry Byrne, University of Florida. 4–5 weeks old male AKR/J mice were obtained from Jackson Laboratories Massachusetts, USA.

Methods

Nanoparticle Formulation

Nanoparticles were made with chitosan and DNA as described before [24]. Briefly, 10 μg of plasmid was added to 100 μl of sodium sulfate and heated to 55° C. Chitosan (0.02%) was also heated to the same temperature and 100 μl of chitosan was added to the DNA-sodium sulfate solution while vortexing at high speed for 20 sec. Particles were examined immediately under light microscope and stored at room temperature Particle Characterization The particles were characterized by size and zeta-potential using a Zetasizer 3000, Malvern Instruments Inc., Massachusettes, USA. The number distribution of particle size as analyzed by the zetasizer and the zeta-potential (pH 5.7) as measured in an aqueous dip cell was used for quality control of the nanoparticles. These particles were further characterized by transmission and scanning electron micrography. For TEM freshly prepared particles were placed on a glow discharged carbon grid, allowed to sit for a few minutes and then air-dried. The grid rotary shadowed at 7 degrees with plantinum. A Zeiss transmission electron microscope was used to visualize the particles. For SEM, cells were grown on coverslips and incubated with nanospheres for 10 min. Following incubation they were fixed, dehydrated in graded ethanol, critical point dried for several cycles and sputter coated with platinum. The particles on cell surface were than visualized through a scanning electron microscope.

Gene Expression

AKR/J mice were fed with either chitosan-DNA nanoparticles containing the LacZ gene (p43LacZ) or with naked plasmid DNA (p43LacZ) using animal feeding needles. Five days later the animals were sacrificed and their stomachs and small intestines were surgically removed. The whole tissues were stained with 4-chloro-5-bromo-3-indolyl-β-galactoside (X-Gal) according to standard protocols. Following overnight staining in a humidified chamber, the tissues were photographed at Pathology Photography, Johns Hopkins Hospital. The pictures were scanned into a computer and adjusted equally for brightness and contrast using Adobe Photoshop. The tissues were then frozen in OCT and cut into thin sections. The sections were counter stained with nuclear fast red and visualized under a light microscope equipped with a digital camera. Pictures were adjusted equally for brightness and contrast in Adobe Photoshop.

Immunization

AKR/J mice were divided into different experimental groups and immunized orally with various formulations using animal feeding needles (Fisher Scientific Inc., USA) attached to a one ml syringe. Each mouse was fed with a ~50 μg DNA dose in a volume of 500–900 μl (depending upon the formulations). The anaphylactic protection experiments were repeated with different experimental and control groups. Blood and fecal extract were collected from immunized and control mice to measured secreted IgA levels in fecal extract, serum IgG2a, increase in serum IgE pre vs. post immunization and release of plasma histamine following Ag challenge.

Collection of Serum and Fecal Extract

Blood was collected at 4 weeks (before sensitization) and 7 weeks (immediately after sensitization but before challenge) through tail vein bleeding from different groups of mice. After 30 min to 1 hr at room temperature the blood was centrifuged at 4° C. for 25–30 min and serum (supernatant) was collected and stored at −80° C. until further measurements. Fecal pellets were also collected from the same groups of mice at 3 and 4 weeks after immunization and frozen at −80° C. for further measurements.

Sensitization for Peanut Allergy

All mice were sensitized three times, one week apart, with crude peanut extract. Each sensitization was performed over two consecutive days; first day by oral administration of 1 mg crude peanut extract with 10 μg cholera toxin per mouse and the second day by i.p. administration of 0.5 μg extract per mouse with aluminum hydroxide as adjuvant. In both cases the administration volume was 200 μl per mouse.

ELISA Measurements

ELISA was performed on serum collected pre and spot sensitization to determine IgE and IgG2a levels and on fecal extracts to measure secretory IgA. Briefly, plates were coated with HAS-DNP standards or Arah2 protein (10 μg/ml) at 4° C. overnight. Blocking was performed for 2 hrs at 37° C. with 1% BSA-PBST. Serum samples were pooled for each group, was added in duplicate (1:5 dilution for IgE and 1:20 for IgG2a), and incubated overnight at 4° C. Biotinylated anti-mouse IgA, IgE and IgG2a were added followed by the addition of streptavadin-HRP and TMB substrate. The plates were read at 450 nm in a microplate manager (Bio Rad, USA). For histamine measurements immunized and control mice were challenged with purified Arah2 and after 12–15 min blood was collected from the optic artery and the plasma was assayed for histamine levels using a competive ELISA based histamine kit (Immunotech Inc., USA).

Challenge with Arah2 Protein

First, non-immunized (sensitized) mice were challenged i.p. with 200 μg of Arah2 protein. Anaphylactic reactions were graded at different time points according to previously reported contentions. Briefly the following grading protocol was observed. Anaphylaxis was classified by the following scoring system: 0, no sign of reaction; 1 scratching and rubbing around the nose and head; 2, decreased activity with an increasing respiratory rate, pilar erecti and/or puffing around the eyes; 3, labored respiration, cyanosis around the mouth and tail; 4, slight or no activity after prodding or tremors, convulsion; 5, death.

Vascular Leakage Study

Anaphylactic vascular leakage was measured using Evan's blue assay. Briefly 200 μl of Evan's blue dye was injected into the tail vein of mice and immediately followed by an i.p challenge of 200 μg Arah2. Mice were monitored for 45 min and sacrificed to record effect of anaphylactic vascular leakage as judged by blue color in the extremities. Mice that develop anaphylaxis have blue extremities due to vascular leakage while immunized mice that are protected from anaphylaxis are expected to have no/reduced blue color. Photograph was taken using a Nikon camera and developed as Ektachrome slides. The slide was scanned in, enlarged and adjusted for brightness and contrast using Adobe Photoshop.

Results

Nanoparticle Synthesis and Characterization

Figure 3A:
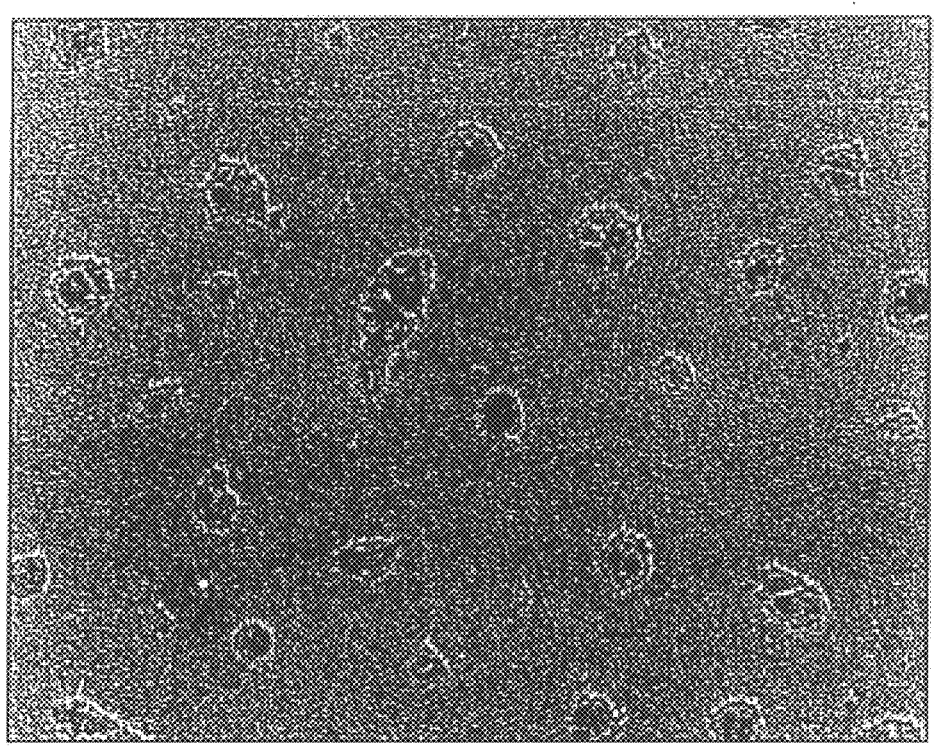
FIG. 3a. shows a transmission electron micrograph of chitoson-DNA nanoparticles. Freshly prepared particles were adsorbed on a glow discharged carbon grid, air-dried and rotary shadowed with platinum at 7°. The grid was viewed under a Zeiss transmission electron microscope (Carl Zeiss Inc. USA). Scale Bar=210 nm.
Figure 3B:
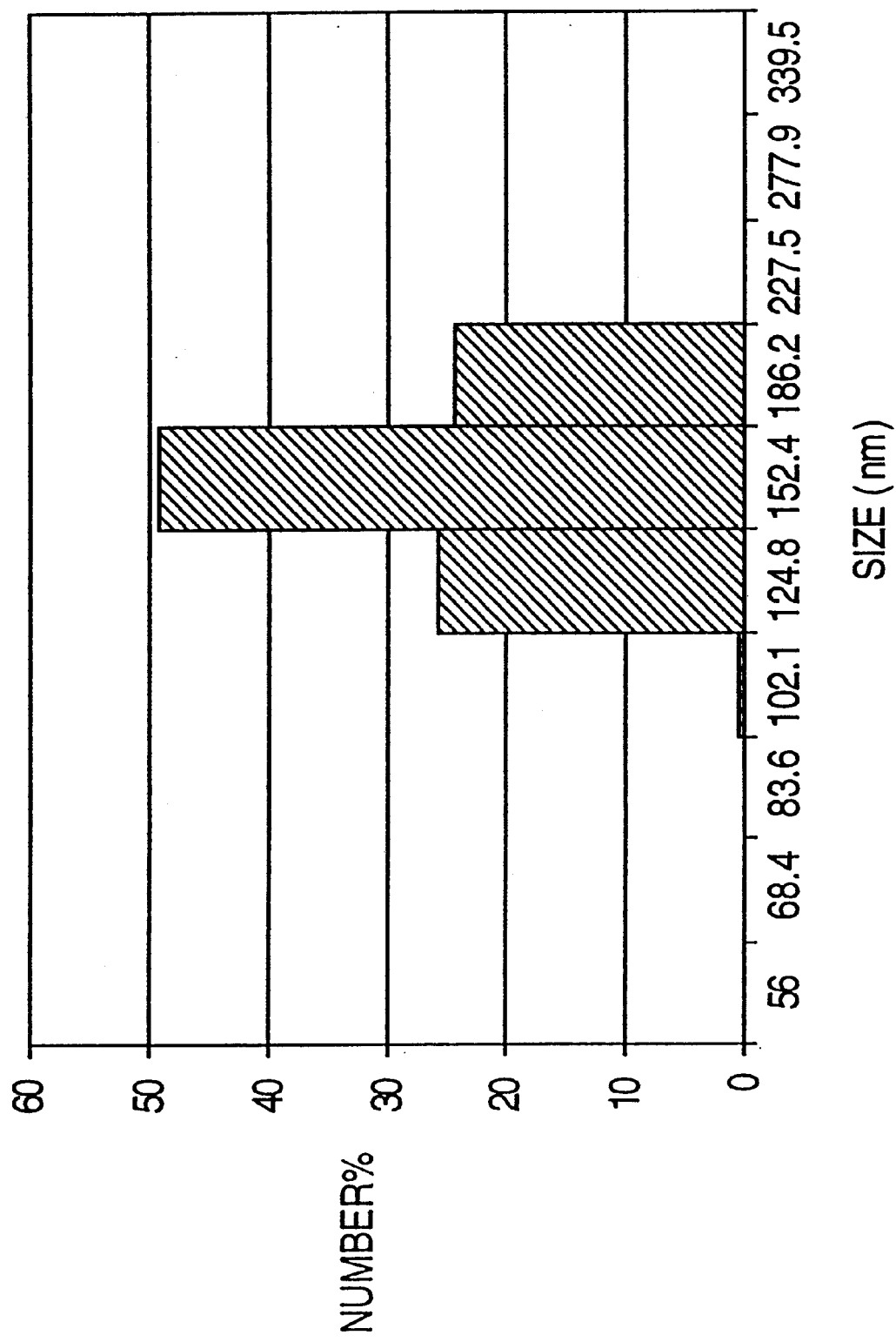
FIG. 3b. shows size distribution of freshly prepared nanoparticles. Size was measured using photon correlation spectoscope (dynamic light scattering) using a Malvern Zetasizer 3000, (Malvern Instruments Inc.) Data was analyzed in the "automatic" analysis mode and plotted as number distribution.

The nanoparticles were synthesized by complexing high molecular weight (~390,000) chitosan with pDNA. Uniform particles were obtained by adding 0.02% chitosan, pH 5.7 (at 55° C.) into pDNA (50 µg/ml in 50 mM sodium sulfate) under high speed vortexing. Transmission and scanning electron microscopy shown that freshly prepared particles are approximately 150–300 nm in size and fairly spherical (FIG. 3a). We have also demonstrated previously [41] that the plasmid is partially protected from DNase degradation in this formulation and its gel migration properties are unchanged by the complexation process (results not shown). Dynamic light scattering (Malvern Zetasizer 3000) measurements shown an unimodal number average particle size distribution between 100–200nm (FIG. 3b). The zeta-potential is approximately +10 mV at pH 5.7 and close to neutral at pH 7. This suggests that the particles are likely to be positively charged at gastric and early duodenal pH but neutral thereafter at more physiological or alkaline pH.

Gene Expression Studies

Figure 4A:
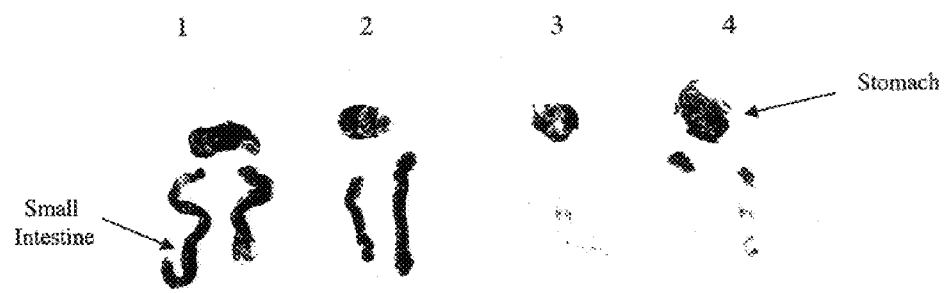
FIG. 4a. Whole tissue staining for LacZ. Only stained sections are shown. The groups are:
1: High molecular weight chitosan—p43LacZ nanospheres, 40 μg per mouse
2. High molecular weight chitosan—p43LacZ nanospheres, 100 μg per mouse
3. Naive (PBS fed)
4. Naked DNA (p43LacZ)
Figure 4B:
FIG. 4b. Histological sections from tissues of 1 (in FIG. 2a). The nucleic were counter stained with nuclear fast red.

To examine the expression and the distribution of transduced genes following oral DNA delivery, AKR/J mice were fed with either chitosan-DNA nanoparticles containing the LacZ gene (p43LacZ) or with naked plasmid DNA (p43LacZ). FIG. 4a shows the tissue expression of bacterial β-galacotosidase (LacZ) in the stomach and small intestine five days after the oral administration. The stained sections represent, on average, 10% of the whole small intestine. While naive and naked DNA fed mice show some background staining, mice fed with the nanoparticles clearly exhibited a higher level of gene expression in both the stomach and the small intestine. FIG. 4b shows frozen sections of the whole tissue (shown in 4a) counter-stained with nuclear fast red. Historically it appears that only epithelial cells in both the stomach and small intestine are strongly stained with X-gal. No staining of hematopoietic cells was observed although immunohistochemistry may not be sensitive enough to identify few transfected immune cells.

Anti-Arah2 Antibody Response

Figure 5A:
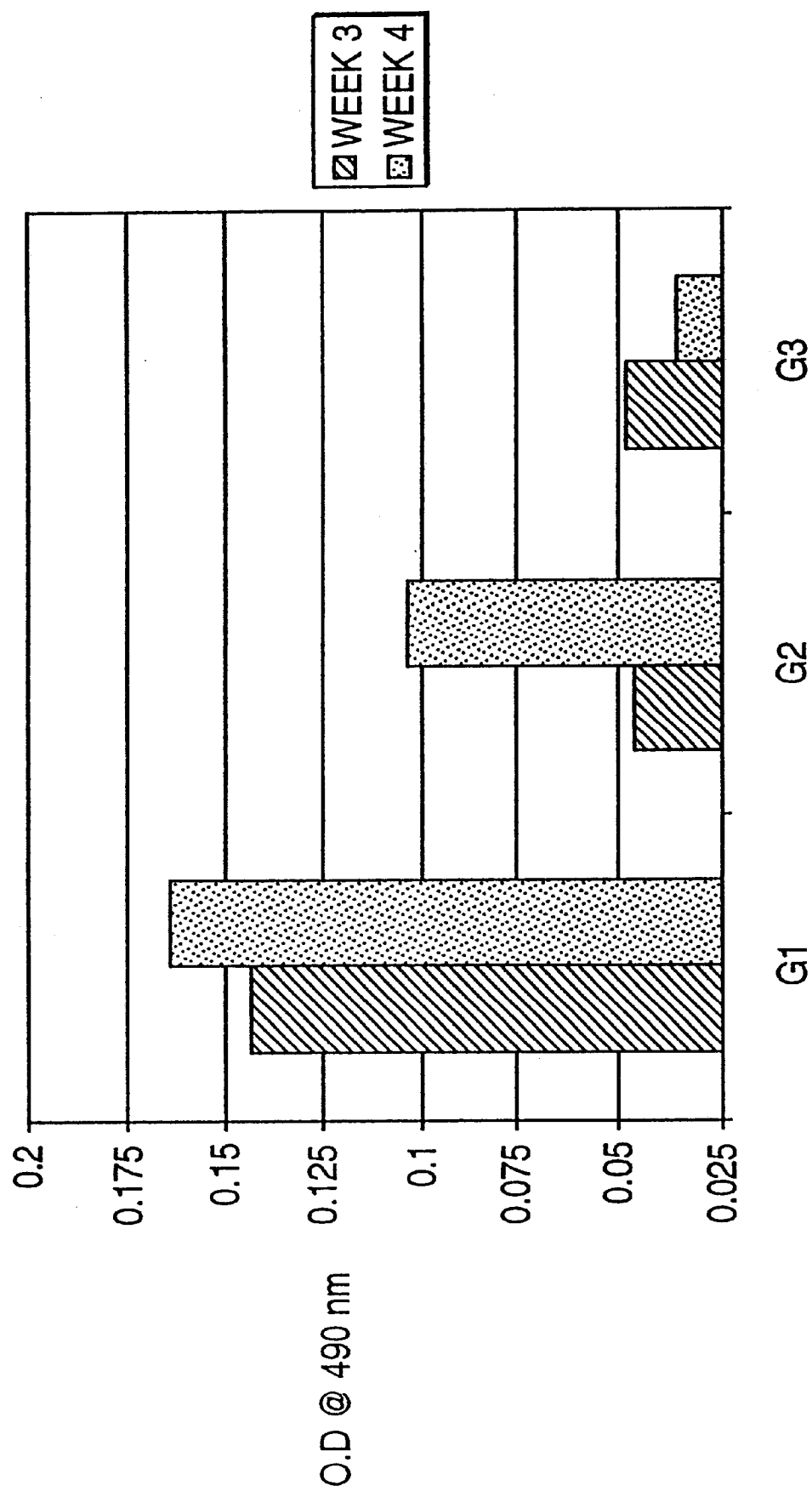
FIG. 5a. shows Anti-Arah2 IgA response in fecal extract 3 and 4 weeks after first immunization. O.D values of 490 nm are reported here for undiluted sample (supernatant of 100 mg/ml fecal pellets dissolved in PBS as described in Methods). Each bar represents values of pooled samples from eight mice (five in case of negative controls).
Figure 5C:
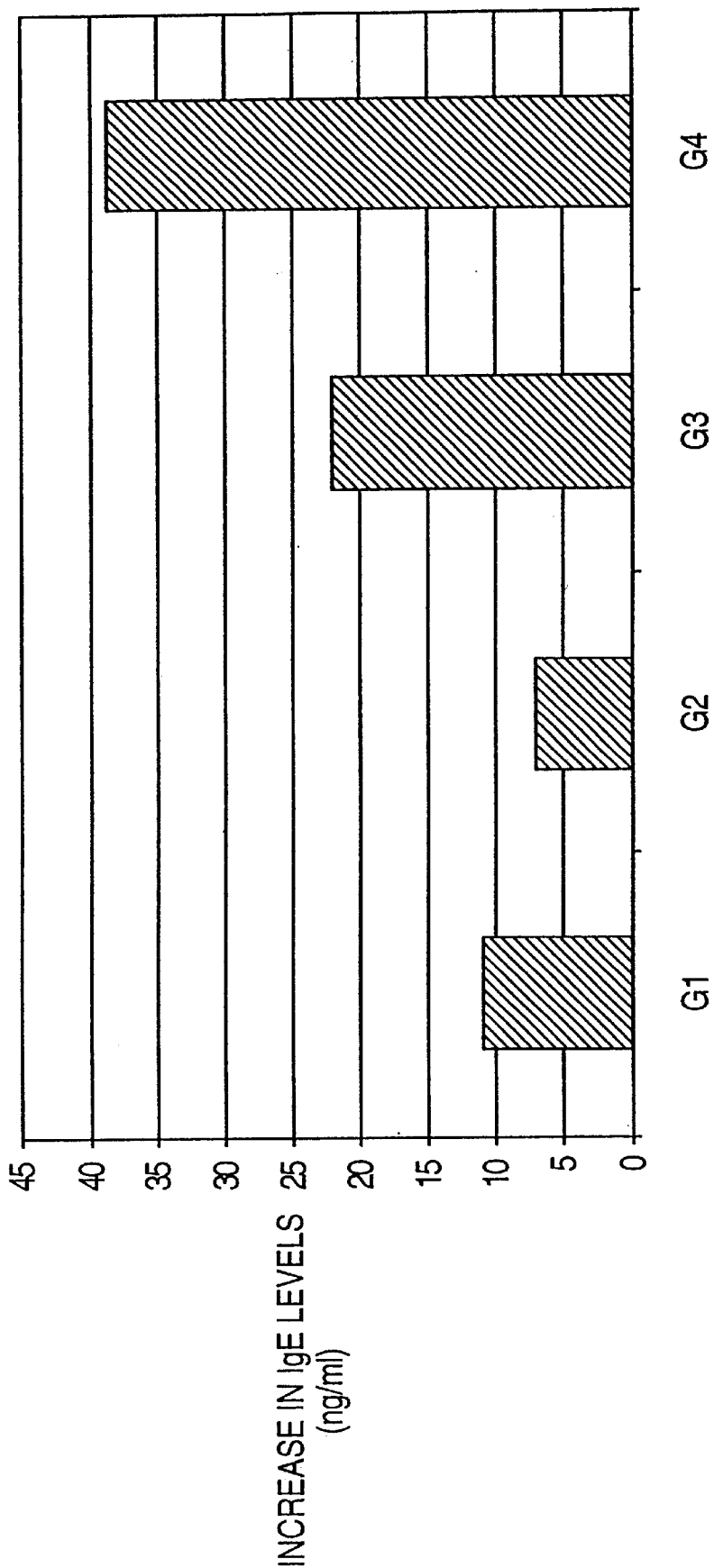
FIG. 5c. shows increase in serum anti-Arah-2 IgE following sensitization. Serum was collected from the same animals 4 weeks after first immunization (before sensitization) and after 3 sensitization. IgE levels were measured (anti-DNP mAb IgE as standards as described in methods) using ELISA. Each bar represents the difference between post and pre-sensitization levels of IgE in pooled serum from 5 mice/group (2 for non-immunized).

To investigate the potential utility of oral nanoparticle-mediated gene immunization to modulate mucosal immune response, a murine model of peanut allergen-induced hypersensitivity was used. It has been demonstrated previously [42] that susceptible strains of mice develop anaphylactic reactions with features similar to those observed in allergic patients. The induction of anaphylaxis was achieved by a combined oral and intraperitoneal (i.p.) sensitization with crude peanut extract and adjuvants [cholera toxin (Ctx) and alum, respectively], followed by i.p. challenge with recombinant Arah2. The hypersensitivity responses include the induction of specific IgE Abs, histamine, vascular permeability, and active systemic anaphylaxis. Using this model, we first examined whether oral delivery of nanoparticles containing pCMV Arah2 was able to induce significant immune response. Four weeks after the first immunization, significant differences in the levels of secreted and serum antibodies were observed between nanoparticle-immunized and control (PBS fed or naive) or naked DNA (pCMV Arah2) immunized mice (FIGS. 5a,b,c). Mice immunized with pCMV Arah2-nanoparticles showed increased levels of secretory IgA in fecal extracts, indicating induction of mucosal immune response. In addition, a significant induction of serum anti-Arah2 IgG2a was observed in nanoparticle-treated animals, indicating a Th1 type T cell response. Of significance is the finding that mice receiving pCMV Arah2 alone (naked DNA) without chitosan show no detectable levels of either fecal IgA or serum IgG2a response at any time points. Since allergic reactions are primarily characterized by an increase in Ag specific serum IgE levels, we also measured the levels of anti-Arah2 serum IgE pre and post sensitization in the immunized and control mice. The increase in serum IgE (post minus pre) was significantly less pronounced in the nanoparticle-immunized groups compared to that in the control or naked DNA immunized animals.

Protection of Immunized Mice Against Arah2 Challenge

FIG. 6 shows the anaphylactic response (in two separate sets of experiments) immediately following i.p. challenge with Arah2 protein in immunized and control mice one week after the third sensitization with PN. Mice receiving sensitization alone without prior immunization or treated with naked DNA (PCMV Arah2) showed physical signs of anaphylaxis within 10–20 min of challenge. The symptoms included slight or no activity after prodding, spasmodic labored breathing with retractions and sometimes death. The severity was ranked 3 to 5 in the scoring system. In contrast, significantly less severe (score 0–2) and delayed anaphylactic responses were seen in chitosan-pCMV Arah2-immunized animals following challenge. All animals recovered in about two hours. In the second set of experiments, when challenged after three sensitization one mouse from each immunized and control groups had sudden death that did not appear to be anaphylactic. This phenomenon was not observed in the first set of challenge experiments. The anaphylactic responses of the remaining mice were similar to the first set of experiments and significant delay and decrease were observed in the nanoparticle-immunized animals as described above.

Plasma Histamine Levels and Vascular Leakage

Histamine release from degranulated mast cells and an increase in vascular permeability are two of the important parameters that characterize anaphylaxis. To examine whether the delayed and less severe PN-induced anaphylactic response seen. in nanoparticle-immunized mice was associated with modulation of histamine release, plasma histamine levels of PN-sensitized, immunized and control mice were assayed 10–15 min following Arah2 challenge. FIG. 7a shows that the histamine level. in the single-dose immunized group was significantly lower than the control group. The nanoparticle-booster group, which showed partial protection, however did not exhibit any significant reduction in histamine level. To determine changes in the level of vascular permeability upon challenge, Evan's blue dye was injected through the tail vein of mice from different experimental groups prior to PN challenge. FIG. 7b shows leakage of Evan's blue from peripheral vasculature (skin and feet). Mice and chitosan-DNA immunized groups show significantly less leakage (i.e. blue color in the footpad and skin) compared to mice from the control and naked DNA immunized groups.

Discussion

This study demonstrates that chitosan-pDNA nanoparticles delivered through the oral route can modify the immune system in mice and protect against food allergen induced hypersensitivity. One of the primary attractions of such an oral vaccine is its potential to generate mucosal as well as systemic immunity. The mucosal immune system is not only geared to protect antigenic entry to the systemic immune system but also be unresponsive to food antigens. Peanut allergy is a "mucosal disease" in which the usually unreactive immune system becomes hypersensitive to the ingested protein and generates strong, abnormal anaphylactic reactions. To protect the host against food allergen-induced anaphylaxis, it is therefor ideal to pre-modify the mucosal immune system. Furthermore, the high patient compliancy in oral administration, especially in children, gives such a delivery system a significant advantage. It has been reported that oral delivery of DNA encapsulated in poly-lactide-co-glycolide (PLG) microspheres can generate immune responses against rotavirus infections. Oral gene delivery for correcting lactose intolerance in a rat model has also been achieved using an adeno-associated-viral vector [45]. Chitosan is an attractive oral gene carrier because of its reported adhesive and transport properties in the gut. Furthermore, chiosan, when complexed with pDNA, can form stable nanoparticles that can be endocytosed by cells in the gastro-intestinal tract. Chitosan being a mucoadhesive polymer, the DNA-nanoparticles might adhere to the gastrointestinal epithelia, transported across the mucosal boundary by M-cells and transect epithelial and/or immune cells in the gut associated lymphoid tissue either directly or through "antigen transfer", as suggested by the β-galactosidase expression following chitosan-p43LacZ delivery. In vitro studies have also shown that chitosan can enhance trans and pericellular transport of drugs across intestinal epithelial monolayers.

The anaphlaxis response in nanoparticle-immunized mice indicates that significant protection can be achieved against allergen challenge by oral delivery of a single dose of plasmid DNA in particle formulation. Unfortunately, the results of a single booster administration were inconclusive indicating that further studies are necessary to investigate the effect of multiple doses and kinetics for an optimal vaccination protocol. The level of plasma histamine in the booster group following challenge would not have suggested anaphylactic protection. The fact that same degree of protection was still observed suggests that the pathogenesis of allergic anaphylaxis in this murine model may be multifactorial.

While the above examples utilize an IgE response to demonstrate principle, this is but one example of a useful response elicited against an antigen. Any type of immune response may be modified by oral vaccination using the nanospheres as taught herein.

Literature Cited

1. Siraganian, R P. 1993. Mechanism of IgE-mediated hypersensitivity. In Allergy: Principles and practice. 4th ed. Middleton, E, Reed C E, Ellis E F, Adkinson N F, Yunginger J W, and Busse W W, Editors. Mosby-year Book, Inc., St. Louis. p105.
2. Sampson, H A. 1993. Adverse reactions to foods. In Allergy: Principles and practice. 4th ed. Middleton, E, Reed C E, Ellis E F, Adkinson N F, Yunginger J W, and Busse W W, Editors. Mosby-year Book, Inc., St. Louis. p1661.
3. Bochner, B S, and Lichtenstein L M. 1991. Anaphylaxis. N Engl J Med. 324:1785–90.
4. Mosmann, T R, and Coffinan R L. 1989. TH1 and TH2 cells: Different patterns of lymphokine secretion lead to different functional properties. Ann. Rev. Immunol. 7:145.
5. Swain, S L, Bradley L M, Croft M, Tonkonogy S, Atkins G, Weinberg A D, Duncan D D, Hedrick S M, Dutton R W, and Huston G. 1991. Helper T-cell subsets: phenotype, function and the role of lymphokines in regulating their development. Immunol. Rev. 123:115.
6. Yocum, M W, and Khan D A. 1994. Assessment of patients who have experienced anaphylaxis: a 3-year survey. Mayo Clin. Proc. 69:16.
7. Kemp, S F, Lockey R F, Wolf B L, et al. 1995. Anaphylaxis: a review of 266 cases. Arch. Intern. Med. 155:1749.
8. Sampson, H A, Mendelson L, and Rosen J R. 1992. Fatal and near-fatal anaphylactic reactions to food in children and adolescents. N. Engl. J. Med. 327:380.
9. Sampson, H A, and Metcalfe D D. 1992. Food allergies. JAMA 268:2840.
10. Bock, S A, and Atkins F M. 1990. Patterns of food hypersensitivity during sixteen years of double-blind, placebo-controlled food challenges. J. Pediatr. 117:561.
11. Yunginger, J W, Sweeney K G, Sturner W Q, Giannandra L A, Teigiand J D, Bray M, Benson P A, York J A, Biedrzycki L, and Squillace D L. 1988. Fetal food-induced anaphylaxis. JAMA 260:1450.
12. Bock, S. 1992. The incidence of severe adverse reactions to food in Colorado. J. Allergy Clin. Immunol. 90:683.
13. Bock, S A, and Atkins F M. 1989. The natural history of peanut allergy. J. Allergy Clin. Immunol. 83:900.
14. Emmett, S., Angus F, Lee P, and Fry J. 1996. Characterization of individuals at high risk of severe peanut anaphylaxis to produce targeted advice and information. RME/F/08:1 (Abstract).
15. Oppenheimer, J J, Nelson H S, Bock S A, Christensen F, and Leung DYM. 1992. Treatment of peanut allergy with rush immunotherapy. J. Allergy Clin. Immunol. 90:256.
16. Wang, Q F, Li X M, Schofield B H, Burks A W, Bannon G A, Huang S K, and Sampson H A. 1997. Peanut allergen-induced anaphylactic response in sensitized mice. J. Allergy Clin. Immunol. 99:480 (Abstract).
17. Snider, D P, Marshall J S, Perdue M H, and Liang H. 1994. Production of IgE antibody and allergic sensitization of intestinal and peripheral tissues after oral immunization with protein Ag and cholera toxin. J. Immunol. 153:647.
18. Lycke, N, Severinson E, and Strober W. 1990. Cholera toxin acts synergistically with IL-4 to promote IgG1 switch differentiation. J. Immunol. 145:3316.
19. Munoz, E, Zubiaga A M, Merrow M, Sauter N P, and Huber B T. 1990. Cholera toxin discriminates between T helper 1 and 2 cells in T cell receptor-mediated activation: role of cAMP in T cell proliferation. J. Exp. Med. 172:95.
20. Davis, H L, and Whalen R G. 1995. DNA-based immunization. In Molecular and cell biology of human genetic therapeutics. Dickson G, Editor. Molecular and cell biology of human disease Series 5. Wright D J M, and Archard L C, Series Editors. Chapman & Hall, Inc. p368.
21. Wang, B, Ugen K E, Srikantan V, Agadjanyan M G, Dang K, Refaeli Y, Saito A I, Boyer J, Williams W V, and Weiner D B. 1993. Gene inoculation generates immune responses against human immunodeficiency virus type I. Proc. Natl. Acad. Sci. USA 90:4156.
22. Davis, H L, Michel M-L, and Demeneix B A. 1993. DNA based immunization for hepatitis B induces continuous secretion of antigen and high levels of circulating antibody. Hum. Mol. Genet. 2:1847.
23. Tascon, R E, Colston M J, Ragno S, Stavropoulos E, Gregory D, and Lowrie D B. 1997. Vaccination against tuberculosis by DNA injection. Nature Med. 2:888.
24. Waisman, A, Ruiz P J, Hirschberg D L, Gelman A, Oksenberg J R, Brocke S, Mor F, Cohen IR, and Steinman L. 1997. Nature Med. 2:899.
25. Wolff, J A, Ludtke J J, Acsadi G, Williams P, and Jani A. 1992. Long-term persistence of plasmid DNA and foreign gene expression in mouse muscle. Hum. Mol. Genet. 1:363.
26. Montgomery, D L, Shiver J W, Leander K R, Perry H C, Friedman A, Martinez D, Ulmer J B, Donnelly J J, and Liu M A. 1993. Heterologous and homologous protection against influenza A by DNA vaccination: optimization of DNA vectors. DNA cell biol. 12:771.
27. Fynan, E F, Webster R G, Fuller D H, Haynes J R, Santoro J C, and Robinson H L. 1993. DNA vaccines:

28. Robinson, H L, Hunt L A, and Webster R G. 1993. Protection against a lethal influenza virus challenge by immunization with a haemagglutinin-expressing plasmid DNA. Vaccine 11:957.
29. Pardoll, D M, and Beckerleg A M. 1995. Exposing the immunology of naked DNA vaccines. Immunity 3:165.
30. Hsu, C H, Chua K Y, Tao M H, Lai Y L, Wu H D, Huang S K, and Hsieh K H. 1996. Immunoprophylaxis of allergen-induced immunoglobulin E synthesis and airway hyperresponsiveness in vivo by gene vaccines. Nature Med. 2:540.
31. Hsu, C H, Chua K Y, Tao M H, Huang S K, and Hsieh K H. 1996. Inhibition of an in vivo allergen-specific IgE response in mice by direct gene transfer. Int. Immunol. 8:1405.
32. Raz, E, Tighe H, Sato Y, Corr M, Dudler J A, Roman M, Swain S L, Spiegelberg H L, and Carson D A. 1996. Preferential induction of a Th1 immune response and inhibition of specific IgE antibody formation by plasmid DNA immunization. Proc. Natl. Acad. Sci. USA 93:5141.
33. Burks, A W, Williams L W, Helm R M, Connaughton C, Cockrell G, and O'Brien T. 1991. Identification of a major peanut allergen, Ara h I, in patients with atopic dermatitis and positive peanut challenges. J. Allergy Clin. Immunol. 88:172.
34. Burks, A W, Williams L W, Connaughton C, Cockrell G, O'Brien T, and Helm R M. 1995. Epitope specificity of the major peanut allergen, Ara hII. J. Allergy and Clin. Immunol. 95:607.
35. Wang, B, Ugen K E, Srikantan V, Agadjanyan M G, Dang K, Refaeli Y, Saito A I, Boyer J, Williams W V, and Weiner D B. 1993. Gene inoculation generates immune responses against human immunodeficiency virus type I. Proc. Natl. Acad. Sci. USA 90:4156.
36. T. Friedmann, Human gene therapy—an immature genie, but certainly out of the bottle, Nature Medicine, 2(1996) 144.
37. R. G. Crystal, The gene as the drug, Nature Medicine, 1(1995) 15.
38. R G. Crystal, Transfer of genes to humans: Early lessons and obstacles to success, Science, 270(1995) 404.
39. Z. Q. Xiang, Y. Yang, J. M. Wilson and H. C. Ertl, A replication-defective human adenovirus recombinant serves as a highly efficacious vaccine carrier, Virology, 219(1996) 220.
40. M. R. Knowles, et al., A controlled study of adenoviral-vector-mediated gene transfer in the nasal epithelial of patients with cystic fibrosis, N. Eng. J. Med., 333(1995) 823.
41. E. W. Alton and D. M. Geddes, Gene therapy for cystic fibrosis: a clinical perspective, Gene Therapy, 2(1995) 88.
42. N. J. Caplen, et al., Liposome-mediated CFTR gene transfer to the nasal epithelium of patients with cystic fibrosis, Nature Medicine, 1(1995) 39.
43. M. Cotten and E. Wagner, Non-viral approaches to gene therapy, Current opinion in biotechnology, (1993) 705–710.
44. A. Singhal and L. Huang, Gene transfer in mammalian cells using liposomes as carriers, in Gene Therapeutics: Methods and Applications of Direct Gene Transfer, J. A. Wolff, Editor. 1994, Birkhauser: Boston.
45. J. P. Schonfield and C. T. Caskey, Non-viral approaches to gene therapy, Brit. Med. J., 51(1995) 56.
46. D. Law, et al., Cancer gene therapy using plasmid DNA: Pharmacokinetic study of DNA following injection in mice, Human Gene Therapy, 6(1995) 553.
47. V. Truong, J. R. Williams, J. Hildreth and K. W. Leong, Targeted delivery of immunomicrospheres in vivo, Drug Delivery, 2(1995) 166.
48. P. Golumbek, R. Azhari, E. Jaff, H. Levitsky, A. Lazenby, K. Leong and D. Pardoll, Controlled release, biodegradable cytokine depots: A new approach in cancer vaccine design, Cancer Res., 53(1993) 5841.
49. K. Brown, W. Shao, J. Bathon and K. Leong, Controlled drug delivery to the joints by enzymatically degradable microspheres, MRS Symposium Series, 331(1994) 290.
50. P. I. Rose, Gelatin. Concise Encyclopedia of Polymer Science and Engineering, ed. J. I. Kroschwitz. 1990, New York: Wiley. 430.

What is claimed is:

1. A method of eliciting an immune response in a mammal against an antigen, comprising:

orally administering an immunogenic formulation comprising a solid nanoparticle of less than 5 μm comprising a coacervate of a polymeric polycation and a polyanion, wherein the polymeric polycation is selected from the group consisting of gelatin and chitosan, and wherein the polyanion consists of nucleic acids encoding an antigen, whereby the antigen is expressed and elicits an immune response in the mammal.

2. The method of claim 1, wherein the nucleic acids comprise an expression vector which comprises a promoter operably linked to an oligonucleotide encoding the antigen.

3. The method of claim 1, wherein the antigen is an allergen.

4. The method of claim 1, wherein the antigen is a food allergen.

5. The method of claim 1, wherein the immunogenic formulation is formulated in a food.

6. The method of claim 1, wherein the immunogenic formulation is formulated in a beverage.

* * * * *